US008547552B2

(12) United States Patent
Yu et al.

(10) Patent No.: US 8,547,552 B2
(45) Date of Patent: Oct. 1, 2013

(54) METHOD FOR DETECTION OF ANALYTE IN MICROARRAY OF SAMPLES AND APPARATUS FOR PERFORMING SUCH METHOD

(75) Inventors: Cheung Hoi Albert Yu, Hong Kong (CN); Lok Ting Lau, Hong Kong (CN)

(73) Assignee: Hai Kang Life Corporation Limited, Shau Kei Wah (HK)

( * ) Notice: Subject to any disclaimer, the term of this patent is extended or adjusted under 35 U.S.C. 154(b) by 16 days.

(21) Appl. No.: 13/121,712

(22) PCT Filed: Oct. 9, 2009

(86) PCT No.: PCT/CN2009/001118
§ 371 (c)(1),
(2), (4) Date: Mar. 30, 2011

(87) PCT Pub. No.: WO2010/040278
PCT Pub. Date: Apr. 15, 2010

(65) Prior Publication Data
US 2011/0176135 A1 Jul. 21, 2011

Related U.S. Application Data

(60) Provisional application No. 61/195,764, filed on Oct. 10, 2008.

(51) Int. Cl.
*G01N 21/00* (2006.01)
(52) U.S. Cl.
CPC ..................................... *G01N 21/00* (2013.01)
USPC .......................................... 356/432; 356/433
(58) Field of Classification Search
CPC .................................................. G01N 21/00
USPC ............................................... 356/432–444
See application file for complete search history.

(56) References Cited

U.S. PATENT DOCUMENTS

| 6,361,944 B1 | 3/2002 | Mirkin et al. |
| 6,506,564 B1 | 1/2003 | Mirkin et al. |

(Continued)

FOREIGN PATENT DOCUMENTS

| CN | 1514244 A | 7/2004 |
| CN | 101201346 A | 6/2008 |
| WO | WO 2007/092173 A2 | 8/2007 |

OTHER PUBLICATIONS

He, Nongyue et al; "Chemiluminescent enzyme immunoassay for cardiac troponin I detection-optimizaton of experimental parameters", *Chemical J. of Chinese Universities*, vol. 28, No. 2, pp. 242-245, (Feb. 2007).

(Continued)

*Primary Examiner* — Michael P Stafira
(74) *Attorney, Agent, or Firm* — Leydig, Voit & Mayer, Ltd.

(57) ABSTRACT

A method for detecting a target analyte associated with nano-sized gold- and/or silver-containing detecting labels in a microarray of samples. The labels indicate presence or absence of a target analyte in a sample. The method includes sequentially illuminating at least two sample groups with at least two different monochromatic light beams. The sample groups include (a) a first sample group containing at least one sample potentially containing the target analyte, and (b) a second sample group serving as positive control or negative control. The method also includes (ii) detecting intensity of light reflected, absorbed, or emitted from each of the sample groups when illuminated with each of the monochromatic light beams. (iii) recording groups of values associated with the intensity reflected, absorbed, or emitted light. (iv) comparing the groups of values associated with the sample groups; and (v) determining the presence of the target analyte based on the comparison.

13 Claims, 11 Drawing Sheets

(56) References Cited

U.S. PATENT DOCUMENTS

| | | | |
|---|---|---|---|
| 6,750,016 | B2 | 6/2004 | Mirkin et al. |
| 6,767,702 | B2 | 7/2004 | Mirkin et al. |
| 2003/0013103 | A1* | 1/2003 | Bryan et al. ............... 435/6 |
| 2003/0059820 | A1* | 3/2003 | Vo-Dinh ..................... 435/6 |
| 2004/0107058 | A1 | 6/2004 | Gomes et al. |
| 2004/0239922 | A1* | 12/2004 | Modlin et al. ............ 356/317 |
| 2005/0105091 | A1* | 5/2005 | Lieberman et al. ........ 356/369 |
| 2006/0256332 | A1* | 11/2006 | Sandstrom ................ 356/317 |
| 2008/0064120 | A1 | 3/2008 | Clarke et al. |
| 2008/0137080 | A1* | 6/2008 | Bodzin et al. ............ 356/300 |

OTHER PUBLICATIONS

Shao, Hongxia et al.; "Optimization of clenbuterol detection kit and monitoring metabolism of CL from experiment samples", *J. of Yangzhou Univ. (Agricultural and Life Science Ed.)*, vol. 27, No. 2, pp. 48-51, (Jun. 2006).

Yguerabide, Juan et al.; "Resonance Light Scattering Particles as Ultrasensitive Labels for Detection of Analytes in a Wide Range of Applications", *J. of Cellular Biochemistry Supplement*, vol. 37, pp. 71-81, (2001).

Foultier, B. et al.; "Comparison of DNA detection methods using nanoparticles and silver enhancement", *IEE. Proc-Nanobiotechnol.*, vol. 152, No. 1, pp. 3-12, (Feb. 1, 2005).

\* cited by examiner

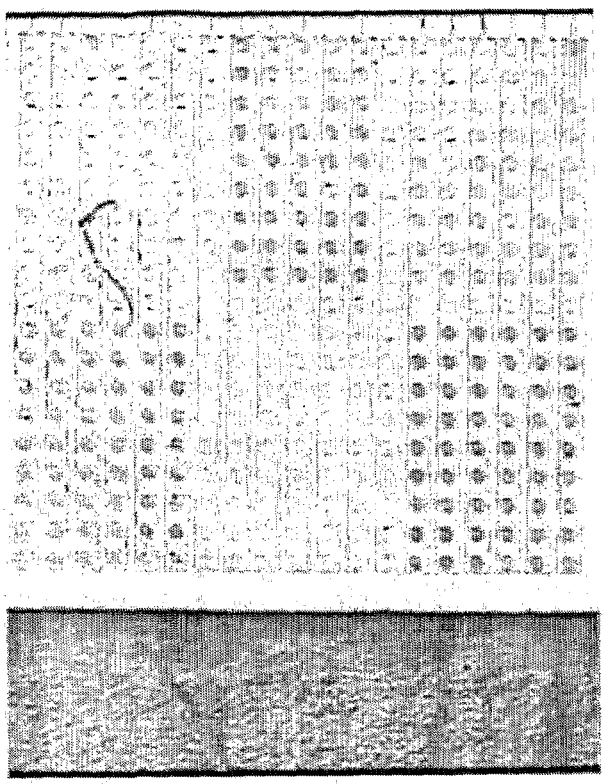
FIG. 2B
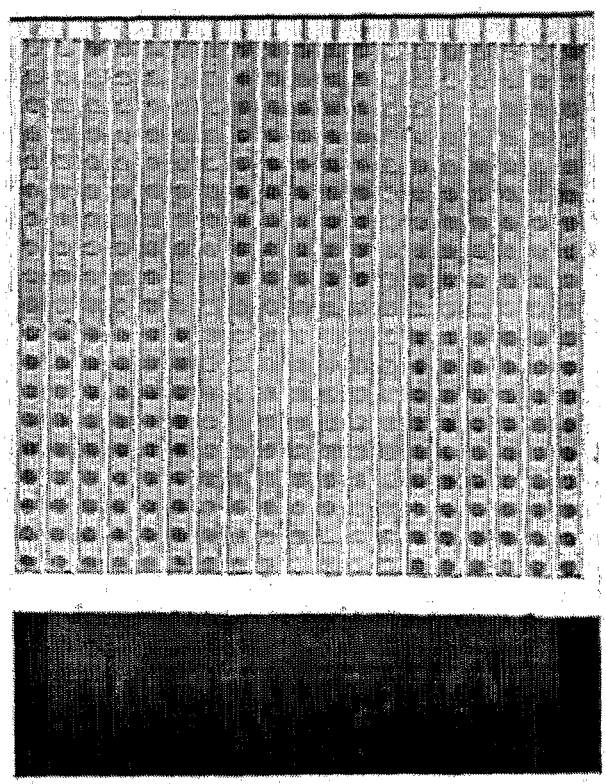
FIG. 2A
FIG. 2

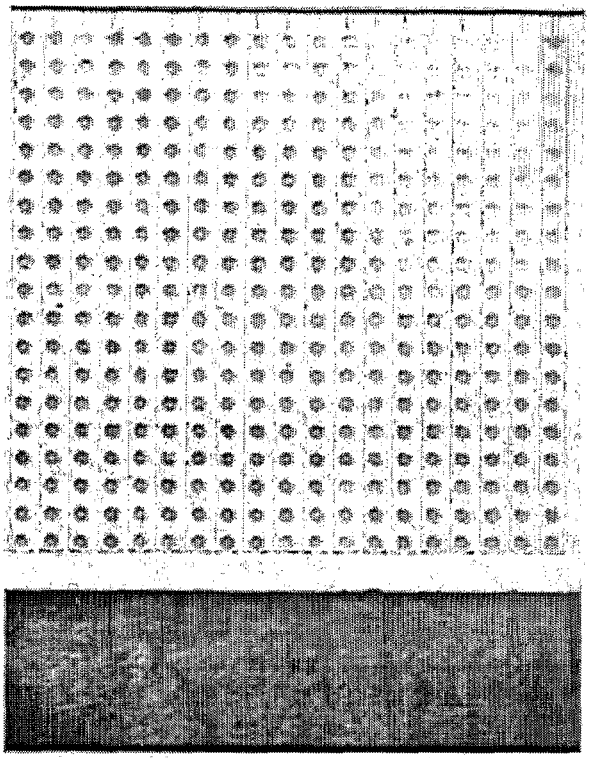
FIG. 3B
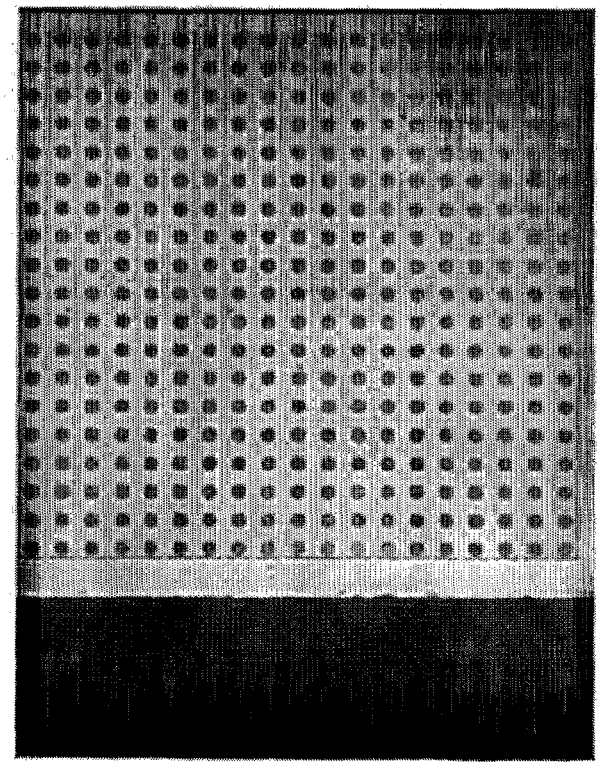
FIG. 3A
FIG. 3

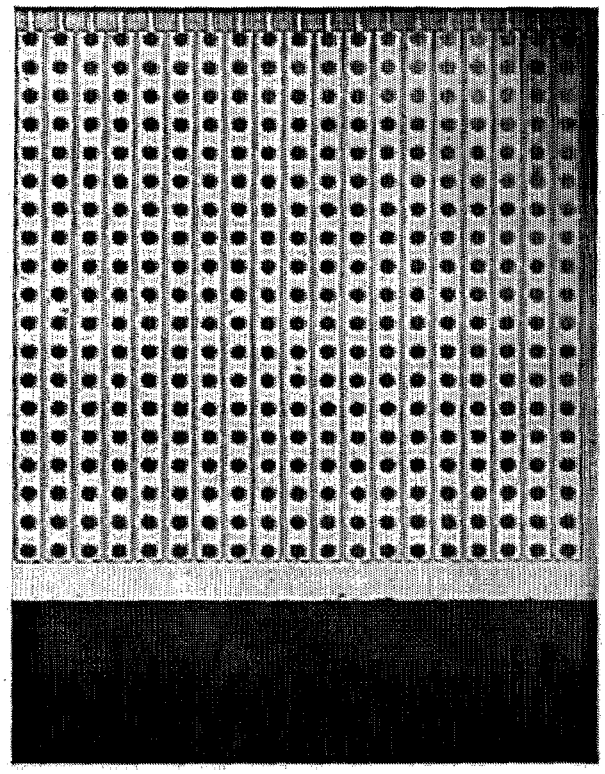
FIG. 4A
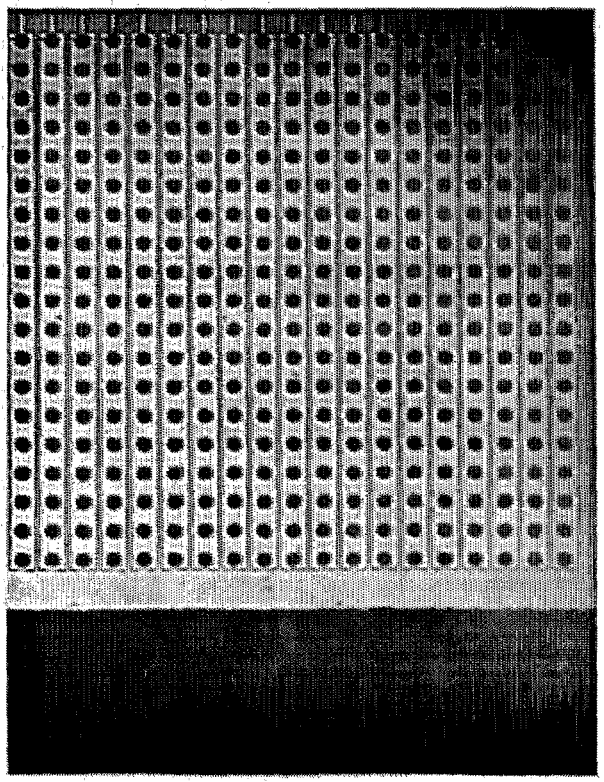
FIG. 4B
FIG. 4

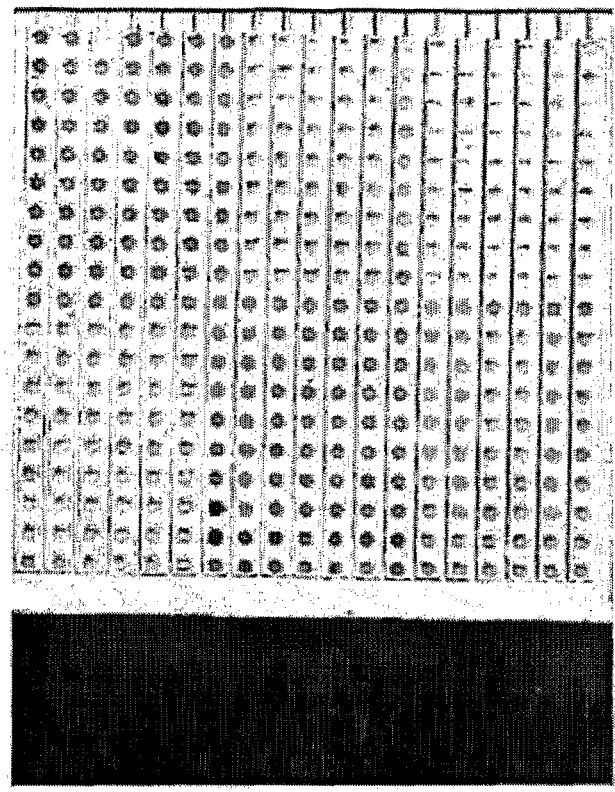
FIG. 5B
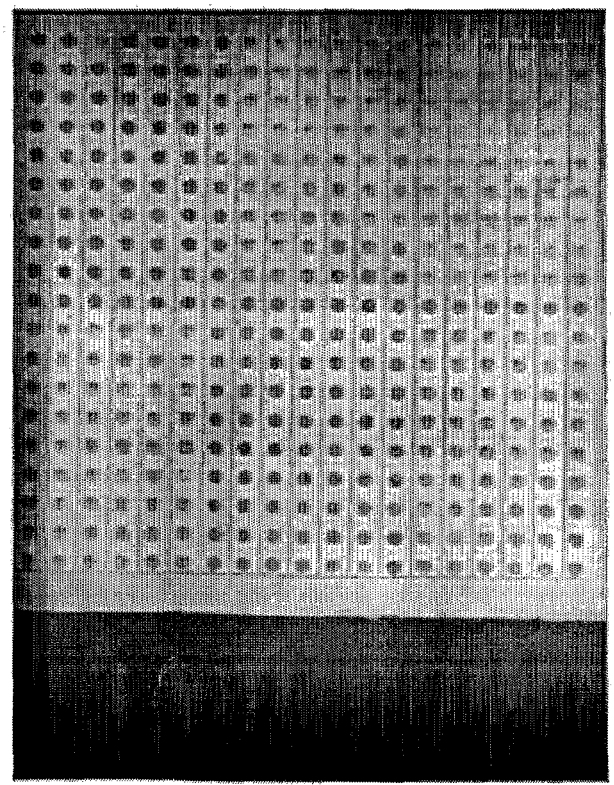
FIG. 5A
FIG. 5

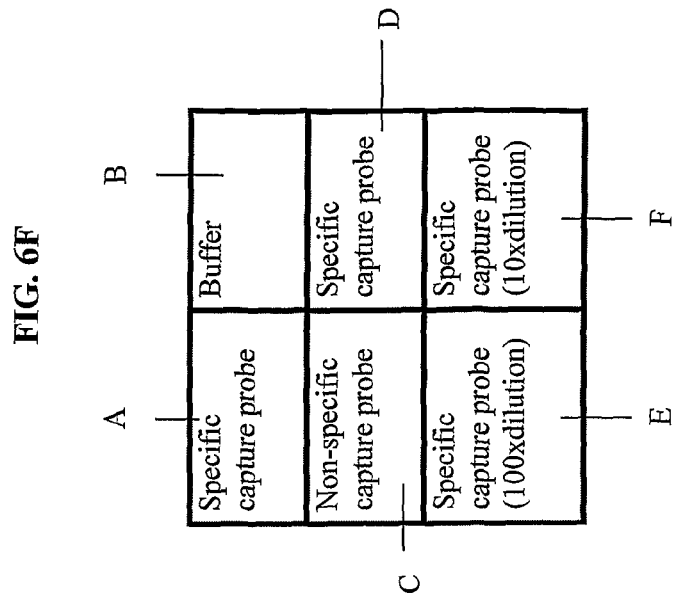
FIG. 6F
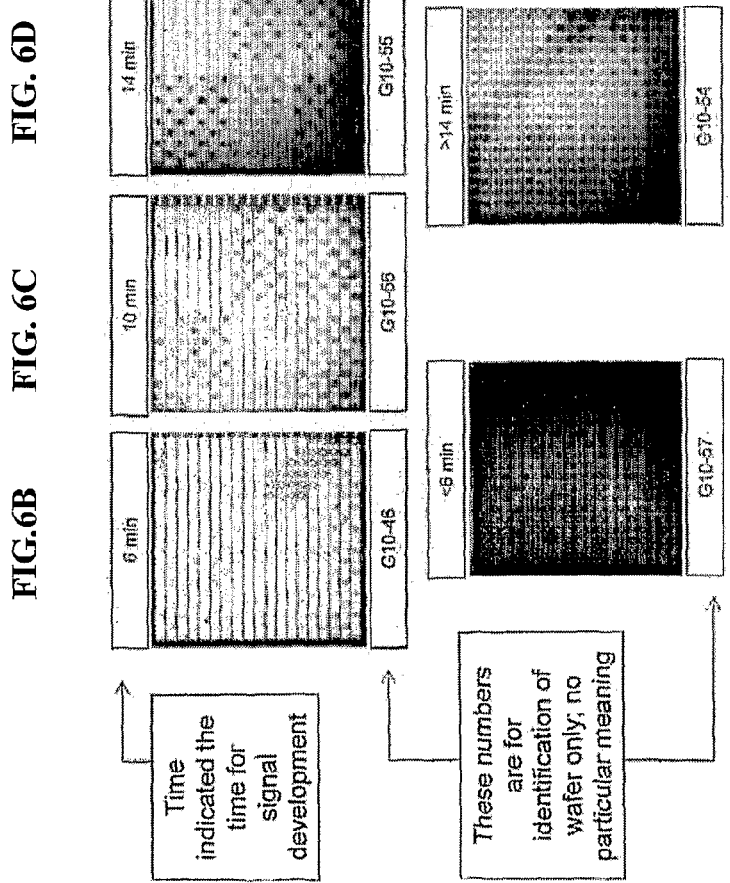
FIG. 6B  FIG. 6C  FIG. 6D  FIG. 6E
FIG. 6A

| 14min | White | | IR | | Red | | Orange | | Yellow | | Green | | Blue | |
|---|---|---|---|---|---|---|---|---|---|---|---|---|---|---|
| Specific group 1/2 | 1.357 | 1.347 | 1.202 | 1.242 | 2.143 | 2.814 | 2.620 | 3.428 | 2.071 | 1.986 | 1.688 | 1.674 | 1.120 | 1.047 |
| Non-specific | 1.120 | | 1.139 | | 1.171 | | 1.277 | | 1.354 | | 1.182 | | 1.065 | |
| Buffer control | 0.986 | | 0.861 | | 0.925 | | 1.148 | | 0.935 | | 0.831 | | 1.151 | |
| Delta | 0.237 | 0.227 | 0.064 | 0.103 | 0.972 | 1.643 | 1.343 | 2.151 | 0.716 | 0.631 | 0.506 | 0.492 | 0.055 | -0.018 |

FIG. 10

METHOD FOR DETECTION OF ANALYTE IN MICROARRAY OF SAMPLES AND APPARATUS FOR PERFORMING SUCH METHOD

FIELD OF THE INVENTION

There present invention is concerned with a method for detecting a target analyte in a sample and an apparatus for performing the method.

BACKGROUND OF THE INVENTION

There are a variety of technologies seeking to provide methods of detecting biological analytes in a sample. For example, U.S. Pat. Nos. 6,361,944, 6,506,564, 6,750,016 and 6,767,702 disclose a method of detecting nucleic acid by observing a change in color when oligo-nucleotides are hybridized to the nucleic acid. Yguerabide et al (Journal of Cellular Biochemistry Supplement 37:71-81 (2001)) discloses the use of resonance light scattering (RLS) particle as labels for analyte detection. Foultier et al (IEE Proc.-Nanobiotechnol., Vol. 152, No. 1, February 2005) discloses the use of fluorescent label technologies in visually detecting the presence or absence of a target analyte in a sample. Despite the availability of these various methods, it has been found that detecting biological analyte by optical means is often unsatisfactory. The present invention seeks to provide an improved method to address this issue, or at least an alternative to the public.

SUMMARY OF THE PRESENT INVENTION

According to a first aspect of the present invention, there is provided a method for detecting target analyte in a sample using electromagnetic wave or monochromatic light, comprising (a) illuminating a sample group with at least one electromagnetic wave or monochromatic light, the sample group including a plurality of samples potentially containing the target analyte, (b) detecting intensity of electromagnetic wave reflected, absorbed or emitted from the sample group when illuminated with the or each electromagnetic wave or monochromatic light, (c) recording group(s) of values associated with the light intensity reflected, absorbed or emitted from the sample group, with the or each group of values associated with each of the respective electromagnetic wave (s) or monochromatic light(s) reflected, absorbed or emitted from the sample group, (d) comparing the group(s) of values associated with the or each electromagnetic wave monochromatic light, (e) selecting the or one of the group(s) of values with a higher signal, and (f) determining the presence or absence of the target analyte based on the selected group of values from step (d). The target analyte can produce a detectable electromagnetic signal when illuminated with an electromagnetic wave or a monochromatic light. The sample may be pre-treated with a signal enhancement agent-containing label to boost the intensity of electromagnetic wave reflected, absorbed or emitted. By comparing the group(s) of values, the group of values which best indicates the presence or absence of the target analyte can be used. In one embodiment, in the above step (a), the sample group may be sequentially illuminated with at least two electromagnetic waves or monochromatic lights.

Preferably, the signal enhancement agent may be a nano-sized particle. More specifically, the nano-sized particle may be a metal particle, a nano-gold particle or a nano-silver particle. The nano-sized particle may be associated with the target analyte by molecular binding.

The method may be used in detecting the target analyte present in a biological sample; the target analyte may be a DNA or a peptide molecule.

Preferably, the monochromatic light may have a frequency from 380 nm to 750 nm. In one embodiment, one of the monochromatic lights is a blue monochromatic light, or, the or one of electromagnetic wave(s) or monochromatic light(s) with a wavelength in the range of 10 nm to 1000 nm. In other embodiments, the or one of the monochromatic lights may be violet, blue, green, yellow, orange or red. Yet in other embodiments, the or one of the electromagnetic waves may be ultra-violet or infra red, or may have a wavelength from 10 nm to 380 nm (ultraviolet), 380 nm to 450 nm (violet), 450 nm to 495 nm (blue), 495 nm to 570 nm (green), 570 nm to 590 nm (yellow), 590 nm to 620 nm (orange), 620 nm to 750 nm (red) or 750 nm to 1000 nm (infra red). The monochromatic light selected may have a wavelength that spans across two of these ranges.

In one embodiment, before determining the presence or absence of the target analyte, the groups of values are compared with each other. However, the groups of values may be compared with a predetermined reference value in such a way that if one or more of the groups of values have a higher value compared to the reference value, the comparison would lead to a determination of a presence of the target analyte, or vice versa. In an alternative embodiment, the groups of values are compared with a group of values obtained from illuminating a group of samples serving as positive control. If the group of values or groups of values are comparable to the group of values from the positive control the comparison would lead to a determination of a presence of the target analyte. Or if the group of values or the groups of values are comparable to the group of values from as a negative control, the comparison would lead to a determination of an absence of the target analyte.

According to a second aspect of the present invention, there is provided a method for detecting nano-sized gold- and/or silver-containing detection labels in a microarray of samples, the labels being indicative of presence or absence of a target analyte in a sample, comprising, (a) sequentially illuminating at least two sample groups with at least two different electromagnetic waves or monochromatic lights with a wavelength from 10 nm to 1000 nm, the sample groups including a first sample group containing at least one sample potentially containing the target analyte, and a second sample group serving as positive control or negative control, (b) detecting intensity of light reflected, absorbed or emitted from each of the sample groups when illuminated with each of the electromagnetic waves or monochromatic lights, (c) recording groups of values associated with the light intensity reflected, absorbed or emitted from the sample groups, with each group of values associated with each of the monochromatic light for each of the sample groups, (d) comparing the groups of values associated with the sample groups and each of the monochromatic lights, and (e) determining the presence or absence of the target analyte based on the comparison in step (d), wherein the monochromatic lights include at least an electromagnetic wave or a monochromatic light with a wavelength in the range of 10 nm to 1000 nm. With the comparison, the group of values which best indicates the presence or absence of the target analyte can be used.

In one embodiment, the at least two sample groups may be illuminated simultaneously with one of the monochromatic lights.

Preferably, the sample groups may include the first sample group containing at least one sample potentially containing the target analyte, the second sample group serving as positive control, and a third sample group serving as negative control. With two comparisons, the reliability of the determination of the presence of absence of the target analyte will be enhanced.

In one specific embodiment, the light reflected, absorbed or emitted from the sample groups may be detected by a CDC camera although any suitable image capturing means may be used.

In one embodiment, after step (c), there is provided a step of taking an averaged value of light intensity of samples in each sample group and generating at least two averaged values associated with each of the monochromatic lights, one averaged value associated with the sample group potentially containing the analyte, and the other or one of the other averaged value(s) associated with the sample group serving as positive control or negative control. The use of an averaged value is advantageous because it can provide a more representative figure for comparison purposes and also the comparison can be made more conveniently. More specifically, there may be provided with a step of taking a differential in absolute value of the averaged values associated with the sample group potentially containing the analyte and the sample group serving as positive control or negative control, thus generating at least two differentials, each associated with the respective monochromatic light. After generating the at least two differentials, there is provided with a step of comparing the differentials with a predetermined differential.

In another embodiment, there may be provided with a step of generating the at least two differentials in absolute value, one of which is associated with the comparison of the averaged values associated with the sample group potentially containing the analyte and the sample group serving as positive control, and the other or one of the other averaged value(s) is associated with the comparison of the averaged values associated with the sample group potentially containing the analyte and the sample group serving as negative control. With this step, there may be provided with a step of generating at least four differentials in absolute value, two of which are associated with values associated with illumination of the sample groups with one of the monochromatic lights and two of the other are associated with values associated with illumination of the sample groups with one of the other monochromatic lights. Then there may be provided with a step of determining which two or at least two of the at least four differentials to use when determining the presence or absence of the target analyte in the sample. According to a third aspect of the present invention, there is provided with a method for detecting nano-sized gold- and/or silver-containing detection labels in a microarray of samples, the labels being indicative of presence or absence of a target analyte in a sample, comprising, (a) sequentially illuminating at least two sample groups with at least two different predetermined monochromatic lights with different frequencies, the sample groups including a first sample group containing at least one sample potentially containing the target analyte, and a second sample group serving as positive control or negative control, (b) detecting intensity of light reflected, absorbed, absorbed or emitted from each of the sample groups when illuminated with each of the electromagnetic waves or monochromatic lights, (c) recording groups of values associated with the light intensity reflected, absorbed or emitted from the sample groups, with each group of values associated with each of the monochromatic lights for each of the sample groups, (d) comparing the groups of values associated with said sample groups and each of said monochromatic light, (e) yielding differential data after step (d), (f) selecting a differential data having the highest value, and (g) determining the presence or absence of the target analyte based on the differential data having the highest value from step (e).

In one embodiment, the at least two sample groups may be illuminated simultaneously with one of the electromagnetic waves or monochromatic lights with a wavelength from 10 nm to 1000 nm.

In another embodiment, the sample groups may include (a) the first sample group containing at least one sample potentially containing the target analyte, (b) the second sample group serving as positive control and (c) a third sample group serving as negative control.

The light reflected, absorbed or emitted from the sample groups may be detected by a CDC camera or any suitable image capturing means.

In another embodiment, there is provided with a step, after step (c), of taking an averaged value of light intensity of samples in each sample group and generating at least two averaged values associated with each of the electromagnetic waves or monochromatic lights, one averaged value associated with the sample group potentially containing the analyte, and the other or one of the other associated with the sample group serving as positive control or negative control.

There may be provided with a step of taking differential in absolute value of the averaged values associated with the sample group potentially containing the analyte and the sample group serving as positive control or negative control, thus generating at least two differentials, each associated with the respective monochromatic light. There may also be provided with a step of comparing the differentials with a predetermined differential.

In another embodiment, there is provided with a step of generating the at least two differentials in absolute value, one of which is associated with the comparison of the averaged values associated with the sample group potentially containing the analyte and the sample group serving as positive control, and the other or one of the other is associated with the comparison of the averaged values associated with the sample group potentially containing the analyte and the sample group serving as negative control. Then there may be a step of generating the at least four differentials in absolute value, two of which are associated with values associated with illumination of the sample groups with one of the monochromatic lights and two of the other are associated with values associated with illumination of the sample groups with one of the other monochromatic lights. There may be further step of determining which two of, or which at least two of, the at least four differentials to use when determining the presence or absence of the target analyte in the sample.

In a preferred embodiment, the sample group may include a plurality of samples arranged in the format of a microarray.

BRIEF DESCRIPTION OF THE DRAWINGS

The present invention will now be described, by way of example only, with reference to the accompanying drawings, in which:—

FIG. 2a and FIG. 2b are photographic images of a microarray of samples under certain conditions;

FIG. 3a and FIG. 3b are photographic images of the same microarray of samples as in FIG. 2a and FIG. 2b under certain conditions;

FIG. 4a and FIG. 4b are photographic images of the same microarray of samples as in FIG. 2a and FIG. 2b under certain conditions;

FIG. 5a and FIG. 5b are photographic images of the same microarray of samples as in FIG. 2a and FIG. 2b under certain conditions;

FIGS. 6a to 6e are photographic images of a microarray of samples taken over a period of time;

FIG. 6f is a table serving as a key to the location of samples in the microarray;

A further set of FIGS. 1 to 11 in color is attached for better illustration.

DETAILED DESCRIPTION OF PREFERRED EMBODIMENTS OF THE PRESENT INVENTION

Detection of some biological samples under certain circumstances has been known to be difficult. For example, when the concentration of the target biological samples is very low, it has been notoriously difficult to detect target samples reliably. Yguerabide et al (Journal of Cellular Biochemistry Supplement 37:71-81 (2001)) proposes the use of resonance light scattering particles as ultrasensitive labels for detection of biological substances. U.S. Pat. No. 6,767,702 proposes a way for the detection of a nucleic acid. Foultier et al (IEE Proc.-Nanotechnology., Vol. 152, No. 1, February 2005) compares different methods of detecting DNA using nano-particles and silver enhancement. (The contents of these references are incorporated herein in this application in their entirety.) Despite the availability of these different methods, there has not been one method which can be generally used to effectively and reliably detect a wide variety of biological samples. The present invention seeks to provide a novel and user friendly way of detecting biological substances. The present invention will now be described by way of the following non-limiting examples and experiments. By way of introduction, it is to be noted that the essence of the present invention is not about the type of samples to be detected, but rather the method of detection. As long as the samples concerned are tagged or can be tagged by a signal enhancement agent, then they may be the subject for detection in accordance with the present invention. It follows that the target sample may be a DNA molecule, a peptide molecule or any organic or inorganic molecule which can be tagged by the signal enhancement agent, e.g. a nano-sized particle, a nano-gold particle, or a nano-silver particle. The signal enhancement is preferably a nano-sized particle. A nano-size particle has a size on the order of $10^{-9}$ m.

EXPERIMENT 1

Figure 1:
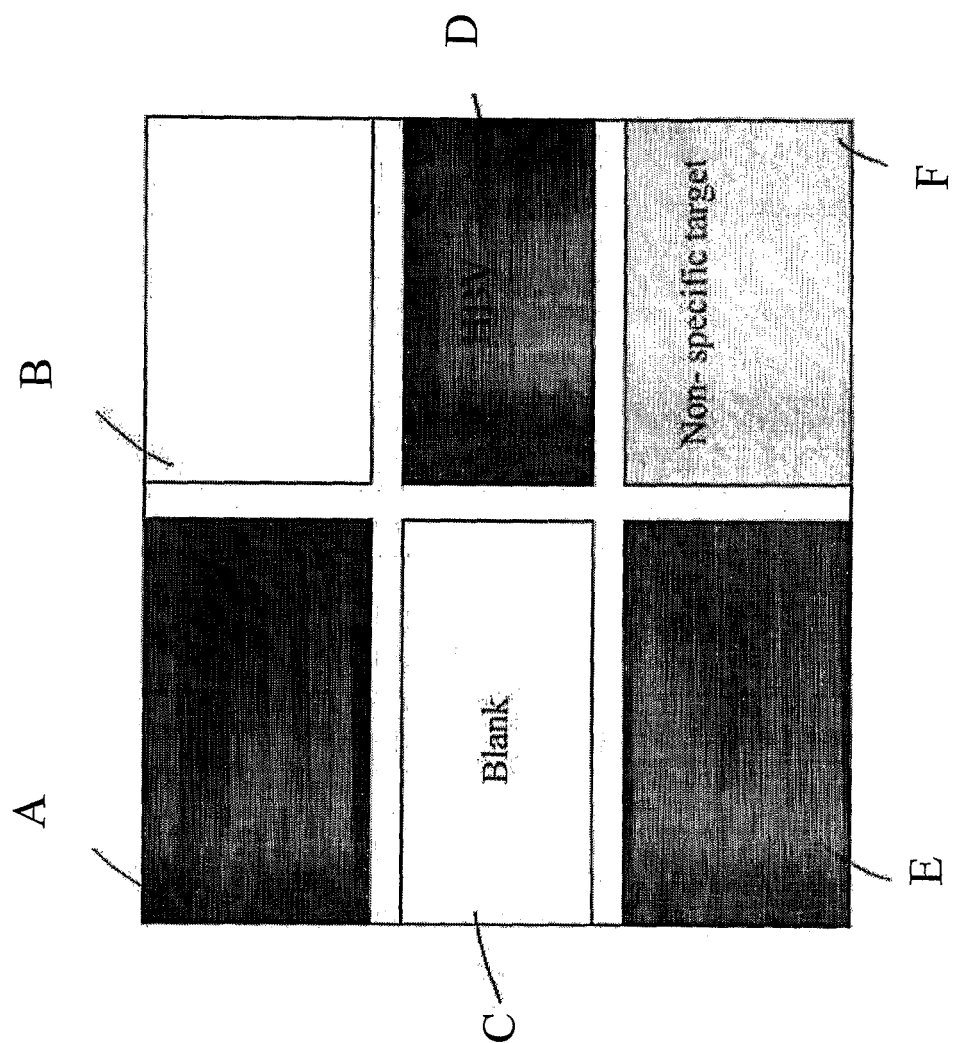
FIG. 1 is a schematic representation of a microarray of samples.

In this experiment, the target analyte was the Hepatitis B virus and the signal enhancement agent was nano-sized gold particle. Hepatitis B virus (HBV) probes tagged with nano-sized gold particle were used as positive control. Specifically, referring to FIG. 1, there is shown a schematic diagram of a microarray of samples on a chip wafer. The chip wafer was spotted according to the pattern as shown in FIG. 1. In particular, the chip wafer was divided into six sections, namely sections A to F. Sections A, D, and E are the dark areas and these areas represent the area of positive control with the Hepatitis B virus probes which have been tagged with the signal enhancement agent. The light grey area, i.e. Section F, was loaded with non-specific targets which served as negative control. The white areas, i.e. Sections B and C, did not contain any spotted sample and they served as negative control. With this configuration, positive result, or darker color, should be observed in regions that were spotted with the HBV probes, while negative result, or minimal color, should be observed in the other regions.

The next step of the first experiment was to ascertain whether, with a view to effectively and accurately ascertain the presence or absence of the HBV probes, any means for investigating the presence of the HBV probes would be advantageous. FIG. 2a and FIG. 2b are images taken by a CDC camera and a B/W CDC camera, respectively, when the same microarray of samples as described above was illuminated with a blue light source with a wavelength from 450 nm to 495 nm. FIGS. 3a and 3b, FIGS. 4a and 4b, FIGS. 5a and 5b are similar to FIGS. 2a and 2b although the images were taken instead when the microarray of samples on the chip wafer was illuminated with a light source of white color, green color with a wavelength from 495 nm to 570 nm and red color with a wavelength from 620 to 750 nm, respectively.

Referring to firstly FIGS. 4a to 4b, although Sections A, D and E did contain the HBV probes and were supposed to yield images with clearly positive result, as can be seen from the figures the images are not clear. Specifically, the contrast between Sections A, D and E and Sections B, C and F is not high. Thus, it means that when the microarray of samples was illuminated by green light, despite the actual presence of the HBV probes (or a real sample possibly containing HBV, or any other sample which may contain a target analyte or biological), it would be difficult to reliably conclude whether there was indeed such target sample. In other words, the use of green color for this particular microarray of samples was not particularly reliable.

Referring to FIGS. 5a to 5b, likewise Sections A, D, and E did contain the HBV probes and were supposed to yield clearly positive result. It is shown that Sections A, D and E do indeed show red dots with a relatively higher contrast to Sections $B_5$ C, F (when compared the corresponding contrast with FIGS. 4a and 4b). It means that the use of red light for detecting the presence of the HBV probes is comparatively advantageous over the use of green light.

Referring to FIGS. 3a and 3b, likewise Sections A, D, and E did contain the HBV probes and were supposed to yield clearly positive result. It is shown that Sections A, D and E do indeed show dots of purple-ish color with a relatively higher contrast to Sections B, C, F (when compared with the corresponding contrast with FIGS. 4a and 4b, and with a similar corresponding contrast to Sections B, C, F when compared with FIGS. 5a and 5b). It means that the use of white light for detecting the presence of the HBV probes is similarly effective when compared to the use of red light but is more effective and advantageous over the use of green light.

Referring to FIGS. 2a and 2b, likewise Sections A, D, and E did contain the HBV probes and were supposed to yield clearly positive result. It is shown that Sections A, D and E do indeed show clear dots of blue color with the highest contrast with Sections B, C and F (as compared with the corresponding contrast between Sections A, D and E and Sections B, C, F of each of FIGS. 3a and 3b, FIGS. 4a and 4b and FIGS. 5a and 5b). This suggests that among the illumination of the enhancement agent tagged HBV samples with blue light, white light, green light and red light, the use of blue light for detecting the presence of the HBV probes is most effective.

EXPERIMENT 2

FIGS. 6a to 11 show data and result of an experiment similar to that shown in FIGS. 1 to 5b and as described above. Specifically, a chip wafer was used and it was similarly divided into six sections, i.e. Sections A to F, with samples including target analyte, positive control and/or negative control loaded therein. Sections A and D were loaded with specific probes. Sections E and F were loaded with specific probes but diluted 100 times and 10 times, respectively. Section C was loaded with non-specific probes and Section B was loaded with only buffer. See FIG. 6f for key. The specific probes were similarly HBV probes. In this experiment, as compared to the experiment as shown FIGS. 1 to 5b, there are however a number of differences. First, reaction was allowed to take place on a chip wafer, and an image of the chip wafer was taken when the reaction had taken place for less than 6 minutes (see FIG. 6a), about 6 minutes (see FIG. 6b), at about 10 minutes (see FIG. 6c), at about 14 minutes (see FIG. 6d) and more than 14 minutes (see FIG. 6e). In principle, as the reaction had progressed, there would be a time range in which the detection of and indication of the presence of the analyte would be particular apparent. In this particular experiment, the chip wafer was illuminated with white light at the different times and the corresponding images were then captured by an image capturing means. The white monochromatic light was a combination of monochromatic lights with wavelength within visible range.

Figure 7:
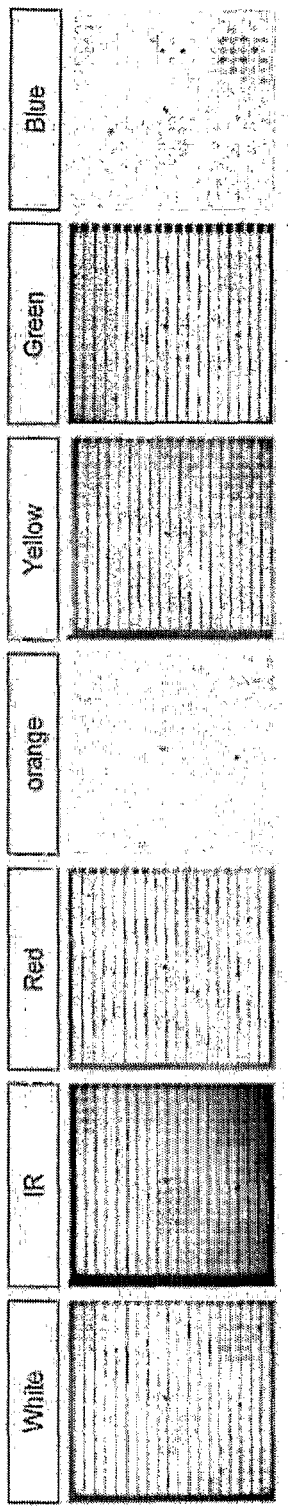
FIG. 7 includes information of images and a table illustrating differences when the microarray is illuminated by light of different color or different frequency; and each of FIGS. 8 to 11 is similar to FIG. 7, except the information relates the microarray illuminated at different times as the reaction in the microarray continues over a period of time.
Figure 8:
Figure 9:
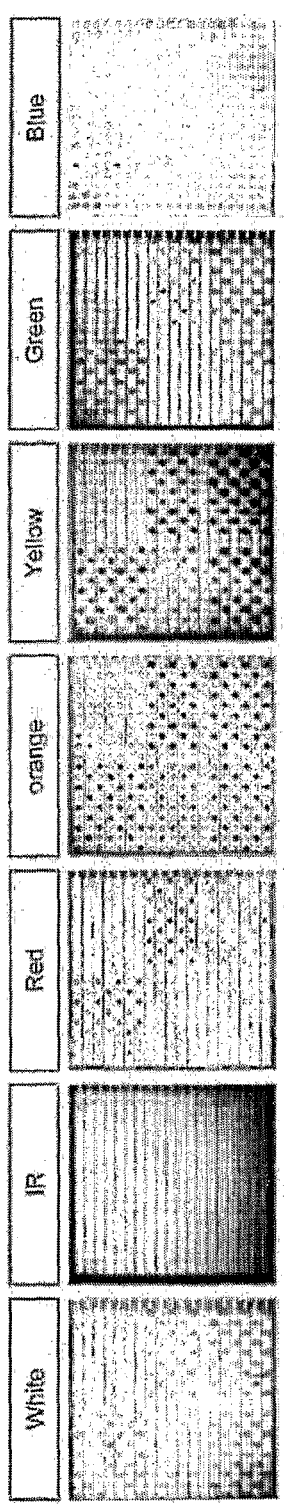

In addition to illuminating the wafer chip with a particular light or monochromatic light (e.g. white monochromatic light as shown in FIGS. 6a to 6f) at a particular time (e.g. less than 6 minutes shown in FIGS. 6a to 6f), the chip wafer was also sequentially illuminated with other monochromatic lights and corresponding images of the chip wafer were captured. FIG. 7 illustrates that the other monochromatic lights included infra red monochromatic light, red color monochromatic light, orange color monochromatic light, yellow color monochromatic light, green color monochromatic light and blue color monochromatic light, and their wavelengths are mentioned above. FIG. 7 also summarizes numerical data reflecting the intensity of the electromagnetic wave or light reflected or emitted from the samples on the chip wafer. In practice, the level of absorption of the electromagnetic wave or light could also be detected. It is thus to be understood that in practice when no electromagnetic wave or light is detected then it suggests that the relevant sample has absorbed all the electromagnetic wave or light illuminated thereon. Alternatively, very often when the electromagnetic wave or light is partially absorbed, the extent of the absorption can be measured by conventional means. It follows that in cases in which the electromagnetic wave or light is absorbed minimally, the level of absorption will be considered insignificantly. In summary, one of the steps of the present invention is to detect the emission, absorption or reflection of electromagnetic wave or light from the respective sample. Since the section with only the buffer loaded therein served as negative control, when comparing the numerical data of the target analyte and that of the buffer, a delta value generated from the comparison was indicative of the presence or absence of the target analyte. FIG. 7 illustrates that the delta value associated with using the blue monochromatic light would provide the best result, which indicates in that in this particular experiment, the use of blue monochromatic light would be most effective in detecting the analyte. FIG. 8 is similar to FIG. 7, although it shows a series of images taken then the reaction had taken place for about 6 minutes on the chip wafer. It is to be noted that the delta value associated with the yellow monochromatic light was highest, which indicates in that in this particular experiment, the use of yellow monochromatic light would be most effective in detecting the analyte at this reaction time. FIG. 9 is similar to FIG. 7, although it shows a series of images taken then the reaction had taken place for about 10 minutes on the chip wafer. It is to be noted that the delta values associated with the orange and yellow monochromatic lights were highest, with the delta value associated with the orange monochromatic light being higher than that of the yellow monochromatic light. This indicates that in this particular experiment, the use of orange monochromatic light would be most effective in detecting the analyte at this reaction time.

FIG. 10 is similar to FIG. 7, although it shows a series of images taken then the reaction had taken place for about 14 minutes on the chip wafer. It is to be noted that the delta value associated with the red monochromatic light was highest, which indicates in that in this particular experiment, the use of red monochromatic light would be most effective in detecting the analyte at this reaction time.

Figure 11:
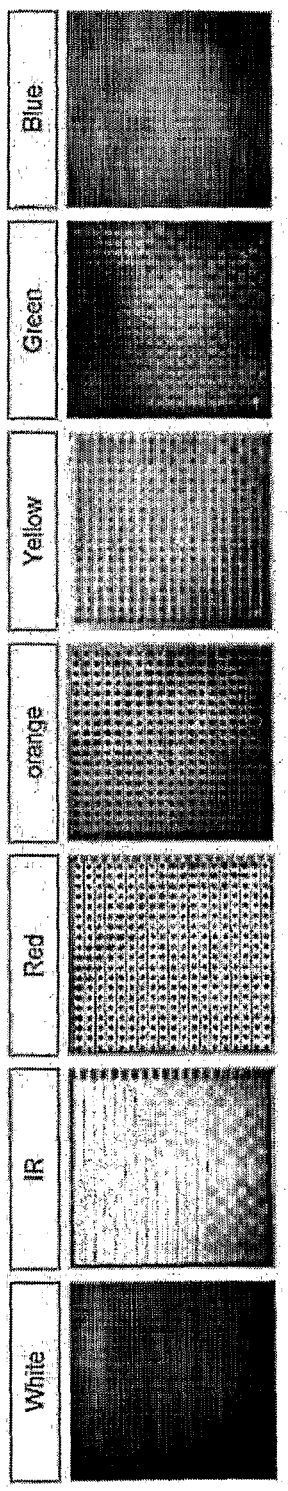

FIG. 11 is similar to FIG. 7, although it shows a series of images taken then the reaction had taken place for more than 14 minutes on the chip wafer. It is to be noted that the delta value associated with the infra red was highest, which indicates in that in this particular experiment, the use of infra red would be most effective in detecting the target analyte at this reaction time.

From the above experiments, it can be concluded that the use of a certain monochromatic light in certain circumstances would be most effective. However, it would be difficult to predict which particular monochromatic light to use at a particular time. Thus, in a preferred embodiment according to one aspect of the present invention, the samples can be sequentially illuminated with a range of different pre-selected monochromatic lights. Data yielding the best delta value can be used to determine the presence of absence of the target analyte.

In the above experiments, the chip wafers were loaded with samples serving positive control and negative control. However, in an alternative embodiment, pre-determined values corresponding to values of positive and/or control may be used for comparison purposes. Appropriate computer software may be provided to conduct the exercise of comparison.

As illustrated in Experiment 1, visual determination of the contrast of the different regions on the chip wafer was made. However, in Experiment 2, the light intensity reflected, absorbed or emitted from the sample was detected and then converted to numerical data digitally.

It should be understood that certain features of the invention, as explained by way of the above experiments, may be provided in combination in a single embodiment. Conversely, various features of the invention, as explained by way of the above experiments, are, for brevity reasons, described in the context of an experiment but may be provided separately or in any appropriate sub-combinations.

The invention claimed is:

1. A method of detecting a target analyte in a plurality of samples in a sample group using monochromatic light, the method comprising:
   treating at least some of the samples of the sample group with nano-sized particles associated with the target analyte by molecular binding as a signal enhancement agent-containing a detection label, wherein each sample potentially contains the target analyte;
   illuminating the samples of the sample group with monochromatic light;

detecting intensity of light reflected from each sample of the sample group when illuminated with the monochromatic light;

recording groups of values associated with the intensity of the light reflected from each sample of the sample group and detected, with the groups of values, or each of the groups of values associated with the light reflected, or emitted from the sample group and detected;

comparing the groups of values associated with the intensities of the light detected;

selecting the one of the groups of values with highest intensity; and determining presence or absence of the target analyte based on the group of values selected.

2. The method as claimed in claim 1, comprising sequentially illuminating the sample group with at least two monochromatic light beams with different wavelengths.

3. The method as claimed in claim 1, wherein the nano-sized particles are metal particles.

4. The method as claimed in claim 3, wherein the nano-sized particles are nano-gold particles.

5. The method as claimed in claim 3, wherein the nano-sized particles are nano-silver particles.

6. The method as claimed in claim 1, wherein the target analyte is present in a biological sample.

7. The method as claimed in claim 1, wherein the monochromatic light has a wavelength in a range from 380 nm to 750 nm.

8. The method as claimed in claim 1, wherein the monochromatic light is blue light.

9. The method as claimed in claim 1, including, in comparing the groups of values, comparing the groups of values to each other or to a predetermined reference value.

10. The method as claimed in claim 1, including, in comparing the groups of values, comparing the groups of values to each other or to a group of values obtained from illuminating a group of samples serving as a positive control.

11. The method as claimed in claim 1, including, in comparing the groups of values, comparing the groups of values to each other or to a group of values obtained from illuminating a group of samples serving as a negative control.

12. The method of claim 1, including illuminating the sample group with monochromatic light, wherein the monochromatic light has a wavelength in a range from 10 nm to 1000 nm.

13. The method of claim 2, including, for each of the monochromatic light beams, individually carrying out the detecting, recording, comparing, and selecting steps and determining the presence or absence of the target analyte based on the group of values selected for each of the monochromatic light beams.

* * * * *